(12) United States Patent
Kim et al.

(10) Patent No.: US 8,771,545 B2
(45) Date of Patent: *Jul. 8, 2014

(54) ABSORBENT AND PASSIVATION LAYER FOR OPTICAL ELEMENT COMPRISING THE SAME

(75) Inventors: Seok Gi Kim, Seongnam-si (KR); Young Sung Suh, Seongnam-si (KR); Kyung Keun Yoon, Seongnam-si (KR)

(73) Assignee: Kolon Industries, Inc., Gwacheon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/637,480

(22) PCT Filed: Jun. 30, 2011

(86) PCT No.: PCT/KR2011/004778
§ 371 (c)(1),
(2), (4) Date: Sep. 26, 2012

(87) PCT Pub. No.: WO2012/002739
PCT Pub. Date: Jan. 5, 2012

(65) Prior Publication Data
US 2013/0020531 A1    Jan. 24, 2013

(30) Foreign Application Priority Data
Jun. 30, 2010 (KR) .................. 10-2010-0063201

(51) Int. Cl.
*B01D 53/28* (2006.01)
*H01L 31/048* (2014.01)
*C07F 5/06* (2006.01)
*H01L 51/52* (2006.01)

(52) U.S. Cl.
CPC ............ *C07F 5/069* (2013.01); *H01L 31/0481* (2013.01); *H01L 51/5259* (2013.01); *Y02E 10/50* (2013.01)

USPC .......................................... 252/194; 556/179

(58) Field of Classification Search
USPC .......................................... 252/194; 556/179
See application file for complete search history.

(56) References Cited

U.S. PATENT DOCUMENTS

| 6,291,699 B1 * | 9/2001 | Birmingham et al. ........ 556/489 |
| 6,362,339 B1 * | 3/2002 | McCormick .................... 546/7 |
| 8,030,644 B2 * | 10/2011 | Shin et al. ....................... 257/40 |
| 2008/0308793 A1 * | 12/2008 | Jeong et al. ................... 257/40 |
| 2011/0245438 A1 * | 10/2011 | Ogane .......................... 526/122 |
| 2012/0261613 A1 * | 10/2012 | Kim et al. ...................... 252/194 |

FOREIGN PATENT DOCUMENTS

| KR | 10-2002-0084377 A | 11/2002 |
| KR | 10-2007-0048995 A | 5/2007 |
| KR | 10-0722464 B1 | 5/2007 |
| KR | 10-0816345 B1 | 3/2008 |

OTHER PUBLICATIONS

Antonio et al., Reactivity of Zirconium Complexes. Organometallics 2002, 21, 2460-2467.*
International Searching Authority, International Search Report of PCT/KR2011/004778 dated Mar. 28, 2012.

* cited by examiner

*Primary Examiner* — Nicole M Buie-Hatcher
*Assistant Examiner* — M. Reza Asdjodi
(74) *Attorney, Agent, or Firm* — Sughrue Mion, PLLC

(57) ABSTRACT

The present invention relates to an absorbent and a passivation layer for an optical element comprising the same, and more specifically to an absorbent that can be applied to a flexible substrate while blocking the inflow of water, and also not blocking light, and a passivation layer for the optical element comprising the same. Also the present invention relates to an absorbent that can maintain a light-emitting property for a long period of time by minimizing damage to the optical element by using the compound synthesized using a non-polar solvent, and the passivation layer for the optical element comprising the same.

19 Claims, 2 Drawing Sheets

ABSORBENT AND PASSIVATION LAYER FOR OPTICAL ELEMENT COMPRISING THE SAME

CROSS REFERENCE TO RELATED APPLICATIONS

This application is a National Stage of International Application No. PCT/KR2011/004778 filed Jun. 30, 2011, claiming priority based on Korean Patent Application No. 10-2010-0063201 filed Jun. 30, 2010, the contents of all of which are incorporated herein by reference in their entirety.

TECHNICAL FIELD

The present invention relates to an absorbent used for an optical element and a passivation layer for an optical element comprising the same.

BACKGROUND ART

Generally, a light-emitting element does not require an external light source, and has a function light emitting by itself. Especially, it has advantages such as a high light-emitting efficiency, excellent luminance and viewing angle, and a quick response speed, but it has a disadvantage that its life is shortened because water or oxygen in the atmosphere is introduced inside the light-emitting element so that electrode is oxidized or a deterioration of element itself is progressed. For this reason, various studies are being carried out to manufacture a light-emitting element that is stable about water and oxygen.

Meanwhile, an organic EL element has a problem that when operating the organic EL element for a certain period, a light-emitting property, such as a light-emitting luminance, a light-emitting efficiency, and a light-emitting uniformity is significantly deteriorated as compared with an initial stage. For example, a cause of deterioration of the light-emitting properties as mentioned above includes an oxidation of electrode due to oxygen permeated inside the organic EL element, an oxidative degradation of organic material caused by a heat during operation, and a denaturalization of organic material. Also, a cause of deterioration of the light-emitting properties further includes a mechanical deterioration of constitution, and for example an interface delaminating of constitution is caused by water and oxygen, and also is generated by causing stress generation on an interface of constitution due to the heat generation and high temperature atmosphere during operation because of a difference between the coefficients of thermal expansion of each constituent.

In order to prevent the above problems, various technologies to seal the organic EL element for suppressing the contact with water and oxygen are researched. For example, as shown in FIG. 1, there is a method for preventing a reaching of water to the organic EL element, comprising: placing a sealing cap 2, in which an absorbent 6 adheres to an inner wall, on a picture element area having an organic EL element including a substrate 1, and a transparent electrode 3, an organic functional layer 4, and a metal cathode electrode 5 formed on the substrate 1; filling a nitrogen gas 9 inside it; and fixing the sealing cap to the substrate 1 by using an adhesive 7.

At this time, various materials are being researched as the absorbent, but alkaline earth metal oxides, such barium oxide (BaO) or calcium oxide (CaO) are widely researched because they can surely capture water molecular and also cannot release water molecular at high temperature not like a water absorbent, such as silica gel or zeolite, that absorbs physically water.

However, the water absorbents have disadvantages that they are particles of an inorganic compound, and require a concave substrate for adhering inside the element so that the element manufactured thickens. Furthermore, the alkaline earth metal oxides are opaque so that it can be applied to a so-called bottom light-emitting display element that emits display light to the substrate 1. However, when the alkaline earth metal oxides are applied to a so-called upper light-emitting display element that emits display light to the sealing cap 2 that is the other side of the substrate 1, a light-emitting can be blocked by the absorbent 6 so that the absorbent 6 should be located to be not entered to an image picture area and the installation place should be provided.

In order to apply the absorbent to the upper light-emitting display element, for example, it can be easily considered that a polymer, such as polyvinyl alcohol and nylon that are transparent and have a property for absorbing water is used as the absorbent. However, the polymer as mentioned above absorbs physically water, and does not have a sufficient water absorbing property as mentioned above.

Furthermore, Japanese Publication Patent No. 2001-357973 discloses using particulate water absorbent that is located to not affect adversely to the light transmission property in the upper light-emitting structure, and Japanese Publication Patent No. 2002-56970 discloses using a plastic substrate having a distributed water absorbents, of which the particle size is smaller than the light emitting wavelength of the organic EL element. However, the inorganic particles are difficult to arrange and evenly distribute as a first particle so that the decrease of the transmittance due to the light scattering cannot be avoided.

In addition, the absorbent produced using the compound synthesized by using an active solvent, such as toluene has a disadvantage that it is left in an optical element in small quantity so that the light emitting property is hindered by causing the phenomenon, such as dark spot, shrinkage, and the like.

DISCLOSURE

Technical Problem

Accordingly, the present invention provides an absorbent, and a passivation layer for an optical element comprising the same, in which the absorbent is to block an inflow of water to the optical element so that a damage of the optical element is minimized and hence the optical element can maintain its light-emitting property for a long period of time.

Furthermore, the present invention provides an optical element including the absorbent and the passivation layer for the optical element.

For this reason, a first preferable embodiment of the present invention provides the absorbent including the compound represented by the following Chemical Formula 1, produced by using an inert solvent:

[Chemical Formula 1]

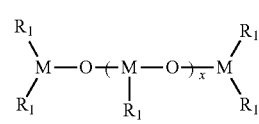

[wherein, all of $R_1$ may be the same or different group to one another as selected from alkyl group, cycloalkyl group, and aryl group that have at least 10 of a number of C; M is selected from trivalent metals; and X is an integer of 1~1000]

The inert solvent according to the above embodiment may be at least one selected from the group consisting of saturated hydrocarbon compound, silicon oil, liquid aromatic petroleum hydrocarbon resin, polyisobutylene, liquid polybutene, and waxes (liquid paraffin).

The absorbent according to the above embodiment may have at least 50% of light transmission measured at 550 nm.

A second preferable embodiment of the present invention provides a passivation layer for the optical element including the compound represented by the following Chemical Formula 1, produced by using an inert solvent:

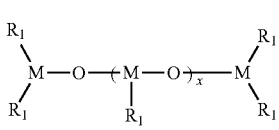

[Chemical Formula 1]

[wherein, all of $R_1$ may be the same or different group to one another as selected from alkyl group, cycloalkyl group, and aryl group that have at least 10 of a number of C; M is selected from trivalent metals; and X is an integer of 1~1000]

The passivation layer for the optical element according to the above embodiment may further include a thermoplastic resin.

The thermoplastic resin according to the above embodiment may have water content of not more than 100 ppm.

The thermoplastic resin according to the above embodiment may be a passivation layer for the optical element having a softening temperature of 50~200° C.

The thermoplastic resin according to the above embodiment may be at least one selected from the group consisting of polyethylene resin, polypropylene resin, polystyrene resin, polyamide resin, acrylic resin, vinyl chloride resin, celluloid resin, phenolic resin, urea resin, melamine resin, alkyd resin, silicone resin, epoxy resin, and urethane resin.

The passivation layer for the optical element according to the above embodiment may be the passivation layer for the optical element having the light transmission of at least 50% measured at 550 nm.

The optical element according to the above embodiment may be the passivation layer for the optical element selected from an organic light-emitting element (OLED), a semiconductor, a liquid crystal display device (LCD), a plasma display device (PDP), and a solar cell.

As a preferable second embodiment, the present invention provides the optical element including the absorbent.

As a preferable third embodiment, the present invention provides the optical element including the passivation layer for the optical element.

DESCRIPTION OF DRAWINGS

The above and other objects, features and advantages of the present invention will become apparent from the following description of preferred embodiments given in conjunction with the accompanying drawings, in which.

TECHNICAL SOLUTION

Figure 1:
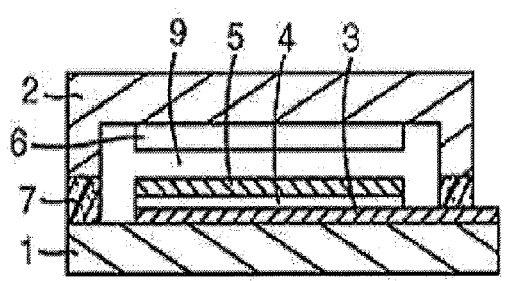
FIG. 1 is a cross-sectional diagram of roughly OLED including a passivation layer for a conventional optical element.

Hereinafter, the present invention will be described in more detail.

The present invention provides an absorbent including the compound represented by the following Chemical Formula 1, produced by using an inert solvent:

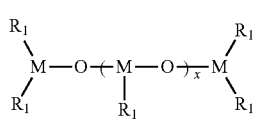

[Chemical Formula 1]

[wherein, all of $R_1$ may be the same or different group to one another as selected from alkyl group, cycloalkyl group, and aryl group that have at least 10 of a number of C; M is selected from trivalent metals; and X is an integer of 1~1000]

A specific example of the alkyl group may include decyl group, undecyl group, dodecyl group, tridecyl group, tetradecyl group, pentadecyl group, hexadecyl group, octadecyl group, nonadecyl group, icosyl group, henicosyl group, docosyl group, and the like.

Furthermore, a specific example of the aryl group may include tolyl group, 4-cyanophenyl group, biphenyl group, o,m,p-terephenyl group, naphtyl group, anthranyl group, phenanthrenyl group, fluorenyl group, 9-phenylanthranyl group, 9,10-diphenylanthranyl group, pyrenyl group, and the like.

Meanwhile, a specific example of the cycloalkyl group may include cyclopentyl group, cyclohexyl group, norbonan group, adamantane group, 4-methylcyclohexyl group, 4-cyanocylcohexyl group, and the like.

The compound represented by the above Chemical Formula 1 is a liquid type, and its ability for absorbing water can be improved by reacting quickly with water as compared with a conventional absorbent of powder type.

Furthermore, the compound represented by the above Chemical Formula 1 can maintain a stable light-emitting property when applying to a light-emitting element because it is not influenced by water for a long period of time.

In addition, the absorbent according to the present invention has at least 50% of light transmission measured at 550 nm thereby emitting light to the top of element so that it can applied to a display, like both sides light-emitting OLED.

Meanwhile, the compound represented by the above Chemical Formula 1 is produced by using an inert solvent so that it can minimize a damage of the optical element by using an inert solvent instead of an active solvent, such as toluene that was traditionally used and hence it can maintain a light-emitting property for a long period of time. That is, it has a disadvantage that when the absorbent including the compound represented by Chemical Formula 1 produced by using the active solvent, such as toluene is applied to the optical element, if the small amount of the absorbent is remained in the optical element, it can cause the dark spot in the optical element, and hence it can hinder the light-emitting property of the optical element.

In order to solve the above problem, the compound represented by Chemical Formula 1 may be preferably produced by using the inert solvent that does not damage the optical element, and the inert solvent may include saturated hydrocarbon compound, liquid aromatic petroleum hydrocarbon resin as a silicon oil, polyisobutylene, liquid polybutene, waxes (liquid paraffin), and the like. A specific example of the inert solvent may include NAPVIS (BP Chemicals), CALSOL 5120 (Naphthenic-substrate oil, Calumet Lubricants Co.), KAYDOL (Paraffin-substrate, White light oil, Witco Co.), TETRAX (Nippon Oil Co.), PARAPOL1300 (Exxon Chemical Company), INDOPOL H-300 (BPO Amoco Co.) that can be purchased, but not limited thereto. Other specific example of the absorbent may include other polyisobutylene homopolymer, polybutylene such as materials to be supplied from Idemitsu Kosan Co., Ltd.,), polybutene, such as materials to be supplied from Nihon Yushi Co., Ltd., and other polybutene polymer. Another specific example of a softening agent may include a trade name, i.e., ESCOREZ 2520 (Liquid aromatic petroleum hydrocarbon resin, Exxon Chemical Company), REGALREZ 1018 (Liquid hydrogenated aromatic hydrocarbon resin, Hercules Ink.), and SYLVATAC 5N (Liquid resin of Modified rosin ester, Arizona Chemical Co.), liquid paraffin, i.e., DN-60LP, DN-100LP, DN-150LP, DN-500LP (DongNam Yuhwa), that are possible to purchase.

Figure 2:
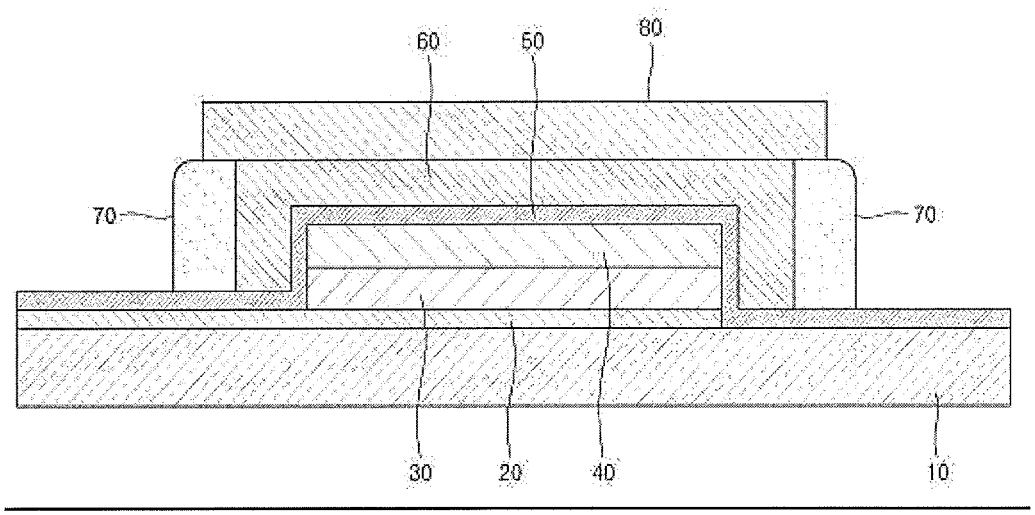
FIG. 2 is a cross-sectional diagram of roughly OLED including a passivation layer for an optical element according to an embodiment of the present invention.

The present invention provides a passivation layer for the optical element including the compound represented by the above Chemical Formula 1 as mentioned above. Referring to FIG. 2, anode 20, an organic layer 30, and a light-emitting cathode 40 are laminated on a substrate 10, and an inorganic water barrier layer 50 is formed on the upper part of the above laminated substrate to form an element part. The passivation layer 60 including the absorbent according to the present invention is formed surrounding at the position surrounding the organic layer 30 and the cathode 40 on the inorganic water barrier layer 50, and a sealing substrate 80 may be installed at the upper part and UV curable sealing agent 70 may be installed around it.

When forming the passivation layer for the optical element, the mixture of the compound represented by the above Chemical Formula 1 and thermoplastic resin may directly coat on the inorganic water barrier layer 50, or may coat on the bottom part of the sealing substrate 80 to adhere together with the inorganic water barrier layer 50. The thermoplastic resin may have not more than 100 ppm of water content and 50~200° C. of softening temperature so that it can prevent an external physical impact by filling the space between the element part and the sealing substrate 80. The thermoplastic resin may include EVA, PS, PP, PE, paraffin, and the like.

Furthermore, if the passivation layer for the optical element has at least 50% of light transmission measured at 550 nm, since it can emit light to the upper part of element, it can apply to a display, such as both light-emitting OLED.

The materials used for forming the substrate 10, the anode 20, the organic layer 30, the light-emitting cathode 40, the inorganic water barrier layer 50, UV curable sealing agent 70, and the sealing substrate 80 can use the known materials to apply to OLED, but not limited thereto.

ADVANTAGEOUS EFFECTS

The passivation layer for the optical element according to the present invention as mentioned above has a high water absorption rate so that it can improve a lifespan of light-emitting element, and also not hinder ductility in a ductile display thereby applying to the ductile display without any problems. Furthermore, it can minimize a damage of the optical element so that it can maintain a light-emitting property for a long period of time.

The passivation layer according to the present invention can be applied to an encapsulation process of a semiconductor, a liquid crystal display (LCD), and a plasma display panel (PDP) as well as the organic light-emitting element (OLED).

BEST MODE

Hereinafter, the present invention will be described with reference to Examples, but the range of the present invention will not be limited to Examples.

Absorbent

EXAMPLE 1

0.2 mol weight of aluminum butoxide (ALDRICH) and 0.6 mol weight of lauric acid (ALDRICH) were mixed to 300 g of liquid paraffin (DN-100LP, DongNam Yuwha); stirred strongly at 800 rpm for 24 hours; and then depressurized at 150 for 2 hours by using an evaporator to obtain the absorbent (R1: lauryl group, X: 400~600, M:Al).

EXAMPLE 2

0.2 mol weight of aluminum butoxide and 0.6 mol weight of dodecane acid (ALDRICH) were mixed to liquid paraffin (DN-100LP, DongNam Yuwha); stirred strongly at 800 rpm for 24 hours; and then depressurized at 150 for 2 hours by using an evaporator to obtain the absorbent (R1: dodecane, X: 400~600, M:Al).

EXAMPLE 3

0.2 mol weight of aluminum butoxide and 0.6 mol weight of oleic acid (ALDRICH) were mixed to liquid paraffin (DN-100LP, DongNam Yuwha); stirred strongly at 800 rpm for 24 hours; and then depressurized at 150 for 2 hours by using an evaporator to obtain the absorbent (R1: oleic acid group, X: 400~600, M:Al).

OLED

EXAMPLES 4~6

The absorbents obtained from Examples 1~3 were coated directly to OLED element to be 20 μm thickness, and then adhered together to the sealing substrate.

COMPARATIVE EXAMPLE 1

0.2 mol weight of aluminum butoxide (ALDRICH) and 0.6 mol weight of oleic acid (ALDRICH) were mixed to 300 g of toluene; stirred strongly at 800 rpm for 24 hours; and then depressurized at 150 for 2 hours by using an evaporator to obtain the absorbent (R1: oleic acid group, X: 400~600, M:Al).

COMPARATIVE EXAMPLE 2

The absorbent obtained from Comparative Example 1 was coated directly to OLED element to be 20 μm of thickness, and then adhered together to the sealing substrate.

Physical properties were measured about OLEDs produced from the above Examples and Comparative Examples as follows, and then the results were shown in the following Table 1.

For measuring the physical properties about the absorbent, the absorbents obtained were coated to the sealing substrate (glass) to be 20 μm of thickness; the solvent was removed at 90° C. for 30 minutes to measure. And, in the case of the lifespan of element, the absorbents obtained were coated to the sealing substrate (glass) to be 20 μm of thickness; the solvent was removed at 90° C. for 30 minutes; adhered together to the element; and then measured as follows:

(1) Water Absorption Rate

A water absorption rate was measured as time passed while storing OLED produced from the above Examples and Comparative Examples in a constant temperature/humidity chamber of 25° C. RH 90%, and an absorption rate was calculated as the following Formula 1.

(Weight after Time passed−Initiate Weight)/Initiate Weight×100  <Formula 1>

(2) Light Transmission

A light transmission was measured at 550 nm before and after water absorption after storing OLED produced from the above Examples and Comparative Examples in a constant temperature/humidity chamber of 25° C. RH 90% for 2 hours.

(3) Lifespan of Element

A light transmission was measured at 550 nm before and after water absorption after storing OLED produced from the above Examples and Comparative Examples in a constant temperature/humidity chamber of 85° C. RH 90%.

(4) Outgassing Test

Figure 3:
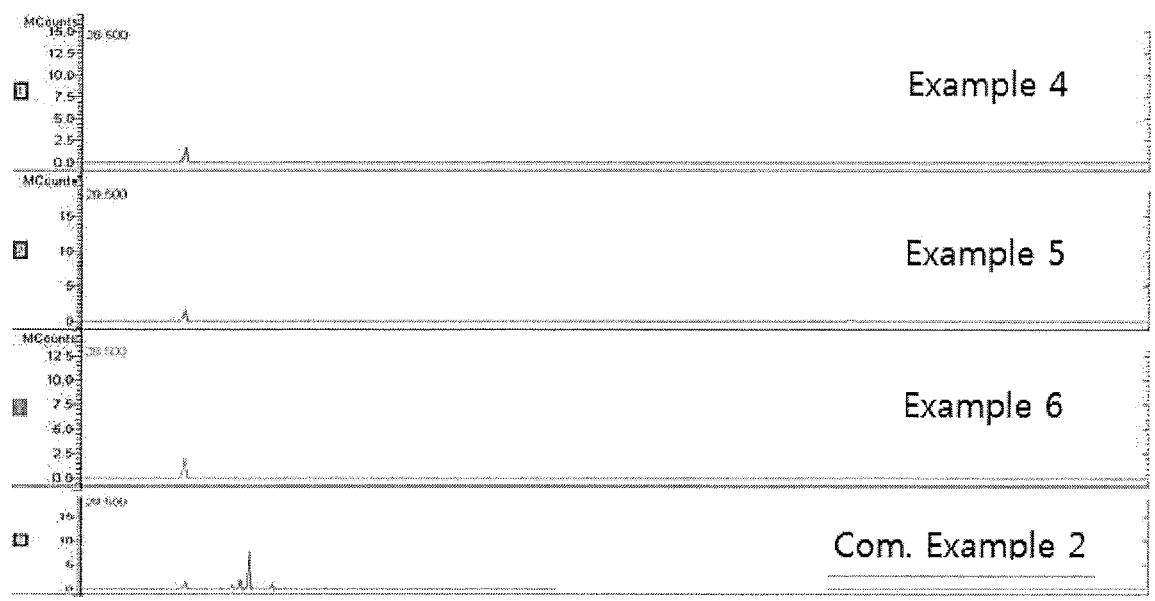
FIG. 3 is a result of out-gassing test about absorbents according to Examples and Comparative Examples of the present invention.

After 5 mg of sample was added into GC-MS vial, and then placed in an oven of 100° C. for 30 min, gas generated was collected and confirmed by using GS Mass, and then the results were shown in the following FIG. 3.

TABLE 1

| Class | Water absorption Rate (%) | | | | | Light Transmission (%) | | Element Lifespan (h) |
| --- | --- | --- | --- | --- | --- | --- | --- | --- |
| | 30 min | 1 h | 2 h | 3 h | 4 h | Before Absorption | After Absorption | |
| Ex. 4 | 15.4 | 17.2 | 18.4 | 18.6 | 18.6 | 97.5 | 96.8 | 610 |
| Ex. 5 | 12 | 14.2 | 15 | 15.2 | 15.3 | 95.7 | 94.2 | 590 |
| Ex. 6 | 19 | 21 | 22.3 | 22.4 | 22.4 | 96.4 | 95.2 | 680 |
| Com. Ex. 2 | 8 | 10 | 14 | 15 | 15 | 96.7 | 95.4 | 430 |

It could be known from the above physical properties that Example 4 to Example 6 had similar light transmission but excellent water absorption rate and element lifespan as compared with Comparative Example 2.

Furthermore, it could be found from Out-gassing test that there were not any remained solvent for Example 4 to Example 6, but a small amount of toluene that was used as the active solvent for Comparative Example 2 was remained.

As mentioned above, if there is a small amount of toluene that is the active solvent, it can cause dark spot in the optical element so that it can hinder the light emitting property of the optical element. Accordingly, it can be known that when the absorbent including the compound produced by using the inert solvent is applied to the optical element, the optical element does not have a damage thereby maintaining the light-emitting property for a long period of time.

[Explanation about Marks]

| | |
| --- | --- |
| 10: Substrate | 20: Anode |
| 30: Organic Layer | 40: Light-emitting Cathode |
| 50: Inorganic Water Barrier Layer | 60: Passivation layer Including Absorbent |
| 70: UV Curable Sealing Agent | 80: Sealing Substrate |

The invention claimed is:

1. An absorbent comprising a compound represented by the following Chemical Formula 1, produced by using an inert solvent:

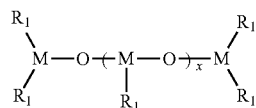

Chemical Formula 1 wherein,
all of $R_1$ may be the same or different group to one another as selected from alkyl group, cycloalkyl group, and aryl group that have at least 10 of a number of C; M is selected from trivalent metals; and X is an integer of 1~1000.

2. The absorbent according to claim 1, Wherein the inert solvent is at least one selected from the group consisting of saturated hydrocarbon compound, silicon oil, liquid aromatic petroleum hydrocarbon resin, polyisobutylene, liquid poly butene, liquid paraffin and waxes.

3. The absorbent according to claim 1, wherein a light transmission measured at 550 nm is at least 50%.

4. A passivation layer for an optical element comprising a compound represented by the following Chemical Formula 1, produced by using an inert solvent:

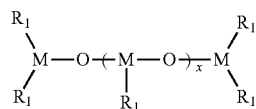

Chemical Formula 1 wherein,
all of $R_1$ may be the same or different group to one another as selected from alkyl group, cycloalkyl group, and aryl group that have at least 10 of a number of C; M is selected from trivalent metals; and X is an integer of 1~1000.

5. The passivation layer for the optical element according to claim 4, further comprising a thermoplastic resin.

6. The passivation layer for the optical element according to claim 5, wherein the thermoplastic resin is at least one selected from the group consisting of polyethylene resin, polypropylene resin, polystyrene resin, polyamide resin, acrylic resin, vinyl chloride resin, celluloid resin, phenolic resin, urea resin, melamine resin, alkyd resin, silicone resin, epoxy resin, and urethane resin.

7. The passivation layer for the optical element according to claim 5, wherein the thermoplastic resin has water content of not more than 100 ppm.

8. The passivation layer for the optical element according to claim 5, wherein the thermoplastic resin has a softening temperature of 50~200° C.

9. The passivation layer for the optical element according to claim 4, wherein a light transmission measured at 550 nm is at least 50%.

10. The passivation layer for the optical element according to claim 4, wherein the optical element is selected from an organic light-emitting element, a semiconductor, a liquid crystal display device, a plasma display device, and a solar cell.

11. An optical element comprising the absorbent according to claim 1.

12. An optical element comprising the passivation layer for the optical element according to claim 4.

13. An optical element comprising the absorbent according to claim 2.

14. An optical element comprising the absorbent according to claim 3.

15. An optical element comprising the passivation layer for the optical element according to claim 5.

16. An optical element comprising the passivation layer for the optical element according to claim 6.

17. An optical element comprising the passivation layer for the optical element according to claim 7.

18. An optical element comprising the passivation layer for the optical element according to claim 8.

19. An optical element comprising the passivation layer for the optical element according to claim 9.

* * * * *